(12) United States Patent
Harding

(10) Patent No.: US 8,094,783 B2
(45) Date of Patent: Jan. 10, 2012

(54) METHOD AND SYSTEM FOR PERFORMING MATERIALS ANALYSIS WITH REFLECTED INELASTIC SCATTER

(75) Inventor: Geoffrey Harding, Hamburg (DE)

(73) Assignee: Morpho Detection, Inc., Newark, CA (US)

( * ) Notice: Subject to any disclaimer, the term of this patent is extended or adjusted under 35 U.S.C. 154(b) by 330 days.

(21) Appl. No.: 12/572,934

(22) Filed: Oct. 2, 2009

(65) Prior Publication Data

US 2011/0081003 A1  Apr. 7, 2011

(51) Int. Cl.
*G01N 23/20* (2006.01)
(52) U.S. Cl. .......................................... 378/88; 378/87
(58) Field of Classification Search .............. 378/6, 7, 378/70, 86–90
See application file for complete search history.

(56) References Cited

U.S. PATENT DOCUMENTS

| | | | |
|---|---|---|---|
| 4,859,002 A * | 8/1989 | Yoshino ........................ 303/156 |
| 5,903,623 A | 5/1999 | Swift et al. | |
| 6,192,101 B1 | 2/2001 | Grodzins | |
| 6,249,567 B1 | 6/2001 | Rothschild et al. | |
| 6,252,929 B1 | 6/2001 | Swift et al. | |
| 6,282,260 B1 | 8/2001 | Grodzins | |
| 6,292,533 B1 | 9/2001 | Swift et al. | |
| 6,356,620 B1 | 3/2002 | Rothschild et al. | |
| 6,421,420 B1 | 7/2002 | Grodzins | |
| 7,551,715 B2 * | 6/2009 | Rothschild et al. ............. 378/57 |
| 7,634,058 B2 * | 12/2009 | Ledoux et al. ................ 378/88 |

OTHER PUBLICATIONS

"Z Backscatter: power, effectiveness and safety", 2009, American Science and Engineering, Inc., pp. 1-4, http://www.as-e.com/products_solutions/z_backscatter.asp.
"Backscatter Technology—SmartCheck advanced personnel inspection", 2009, American Science and Engineering, Inc., pp. 1-2, http://www.as-e.com/products_solutions/smart_check.asp.
"Z Portal Screening System for Cargo and Vehicles", 2009, American Science and Engineering, Inc. 1 page, http://www.as-e.com/products_solutions/portal.asp.
Kortright et al., Center for X-Ray Optics Advanced Light Source: X-Ray Data Booklet, Second Edition, Jan. 2001, U.S. Department of Energy, 2 pages, http://xdb.lbl.gov/Section1/Sec_1-2.html.
Hindeleh et al., The resolution of multipeak data in fibre science, J. Phys. D.:Appl. Phys., 1971 vol. 4, pp. 259-263, Great Britain.
Matscheko et al., Compton spectroscopy in the diagnostic x-ray energy range, Phys. Med. Biol., 1989, vol. 34 (2), pp. 199-208, United Kingdom.

* cited by examiner

*Primary Examiner* — Irakli Kiknadze
(74) *Attorney, Agent, or Firm* — Armstrong Teasdale LLP

(57) ABSTRACT

A method for performing materials analysis of an object using an X-ray system includes generating an X-ray beam using an X-ray source having an anode and acquiring a scatter spectrum from Compton scatter produced when the X-ray beam interacts with the object. The scatter spectrum is acquired using an energy resolving detector. A Compton profile is extracted from the scatter spectrum by processing the scatter spectrum using a control system of the X-ray system. The Compton profile includes peaks at characteristic lines of the anode. The method further includes identifying a characteristic of a material of the object using the Compton profile, and outputting an indication of the characteristic of the material.

20 Claims, 8 Drawing Sheets

METHOD AND SYSTEM FOR PERFORMING MATERIALS ANALYSIS WITH REFLECTED INELASTIC SCATTER

BACKGROUND OF THE INVENTION

1. Field of the Invention

The embodiments described herein relate generally to imaging methods and systems and, more particularly, to imaging methods and systems that use Compton scatter to generate an image.

2. Description of Related Art

During at least some imaging scans using X-rays, a portion of the X-rays are absorbed by an object, another portion of the X-rays are transmitted through the object, and yet another portion of the X-rays are scattered by the object. Back scattering of photons from the object is referred to herein as "Compton scatter," "Compton back scatter," "back scatter," or "reflected inelastic scatter." In at least some known X-ray systems, Compton scatter is used for imaging superficial regions of extended volumes by measuring an intensity of the Compton scatter. The intensity of Compton scattering depends on local electron density, which is similar to the physical density for materials composed of light elements, and can be used to generate images of the scanned object. However, such Compton scatter imaging measures a total reflected X-ray signal without regard to energies of back scattered photons.

At least some known inspection tasks benefit from the capability to differentiate between substances based on their chemical properties. Such a capability is also referred to as molecular specific imaging. One known type of molecular specific imaging is X-ray diffraction imaging, in which Bragg peaks are analyzed to give information on crystal lattice spacings. Bragg peaks are generated using forward coherent scattered photons rather than back scattered inelastic photons. As such, back scattered photons are currently used for electron density imaging, and forward scatter photons are used for molecular specific imaging. Although Compton back scatter is used for intensity imaging, it is desirable to also use Compton back scatter for molecular specific imaging and/or identification.

BRIEF SUMMARY OF THE INVENTION

In one aspect, a method for performing materials analysis of an object using an X-ray system is provided. The method includes generating an X-ray beam using an X-ray source having an anode, acquiring a scatter spectrum from Compton scatter produced when the X-ray beam interacts with the object, wherein the scatter spectrum is acquired using an energy resolving detector, extracting a Compton profile from the scatter spectrum by processing the scatter spectrum using a control system of the X-ray system, wherein the Compton profile includes peaks at characteristic lines of the anode, identifying a characteristic of a material of the object using the Compton profile, and outputting an indication of the characteristic of the material.

In another aspect, an X-ray system for analyzing an object is provided. The X-ray system includes an X-ray source having an anode and at least one source focus. The X-ray source is configured to generate an X-ray beam at the at least one source focus, and the anode is configured to generate characteristic lines. The X-ray system further includes an energy resolving detector positioned with respect to the at least one source focus. The energy resolving detector is configured to record Compton scatter produced from the X-ray beam interacting with the object, wherein the Compton scatter is at an angle to a direction of the X-ray beam. A control system is operationally coupled to the X-ray source and the energy resolving detector. The control system is configured to acquire a scatter spectrum from the Compton scatter using the energy resolving detector, extract a Compton profile from the scatter spectrum by processing the scatter spectrum, wherein the Compton profile includes peaks at the characteristic lines of the anode, and identify a characteristic of a material of the object using the Compton profile.

The embodiments described herein produce a Compton profile of back scatter photons that can provide material specific imaging and/or identification. More specifically, detected Compton scatter is used to generate the Compton profile for identifying a material.

BRIEF DESCRIPTION OF THE DRAWINGS

FIG. 1 is a graph of Compton peak width with respect to scatter angle.

FIG. 2 is a schematic view of an exemplary X-ray system.

FIG. 3 is a schematic view of the X-ray system shown in FIG. 2 shown on an X-Y-Z coordinate system.

FIG. 4 is a flowchart of a method for performing materials analysis with reflected inelastic scatter that may be used with the X-ray system shown in FIGS. 2 and 3.

FIG. 5 is a flowchart of an exemplary extraction process that may be used with the method shown in FIG. 4.

FIG. 6 is a flowchart of an alternative extraction process that may be used with the method shown in FIG. 4.

FIG. 7 is a graph of a Compton scatter spectrum of Beryllium (Be) and Aluminum (Al) that may be generated using the X-ray system shown in FIG. 2 and the method shown in FIG. 5.

FIG. 8 is a graph of a Compton scatter spectrum of a Poly(methyl methacrylate) (PMMA) material and polyethelene that may be generated using the X-ray system shown in FIG. 2 and the method shown in FIG. 5.

DETAILED DESCRIPTION OF THE INVENTION

The embodiments described herein provide Compton back scatter imaging that includes molecular specific identification capability. More specifically, a fundamental physical vector on which the embodiments described herein are based is an electron momentum distribution, which is derived from a measurement of a Compton profile. Further, the synthesis of X-ray imaging and X-ray analysis via the Compton profile greatly extends the utility of Compton back scatter devices for inspection and/or screening. Such Compton back scatter devices can also be used in the analysis and back scatter imaging of plastic components in process monitoring, aircraft inspection, and/or the recycling industry.

The embodiments described herein assume that inelastic scatter induced by monochromatic radiation in a material sample is polychromatic. Such line broadening can be described by a "Doppler effect" originating in bound, thus moving, electrons of which a material consists. Further, as used herein, characteristic X-ray emissions from a material include a series of X-ray spectral lines or characteristic lines, such as Kα lines, with discrete frequencies that are characteristic of an emitting atom, and energy resolution is defined herein as the full width at half maximum (FWHM) of the full energy peak in a pulse height distribution.

Further, the methods described herein include examining back scatter, $K\alpha1$ lines, and $K\alpha2$ lines and performing an energy analysis of the back scatter in a region of the $K\alpha1$ lines and $K\alpha2$ lines. For example, an X-ray source generates the $K\alpha1$ line and the $K\alpha2$ line, the analysis is performed in the region of the $K\alpha1$ line and the $K\alpha2$ line, and distinct shapes of the $K\alpha1$ line and the $K\alpha2$ line to identify a material. Such methods are performed using a high energy resolving detector to acquire the back scatter. As such, the embodiments described herein provide an imaging and/or analysis modality based on energy-resolved inelastic back-scatter to yield a Compton profile. Aspects of the embodiments include a constant angle ($\theta \geqq 150°$) back-scatter measurement topology; a self-normalization of a signal from W $K\alpha$ lines against a continuous region of a spectrum; iterative deconvolution of a $K\alpha1$, 2 doublet structure to derive a Compton profile; and a simple extraction procedure yielding features that are physically relevant to materials characterization.

Figure 1:
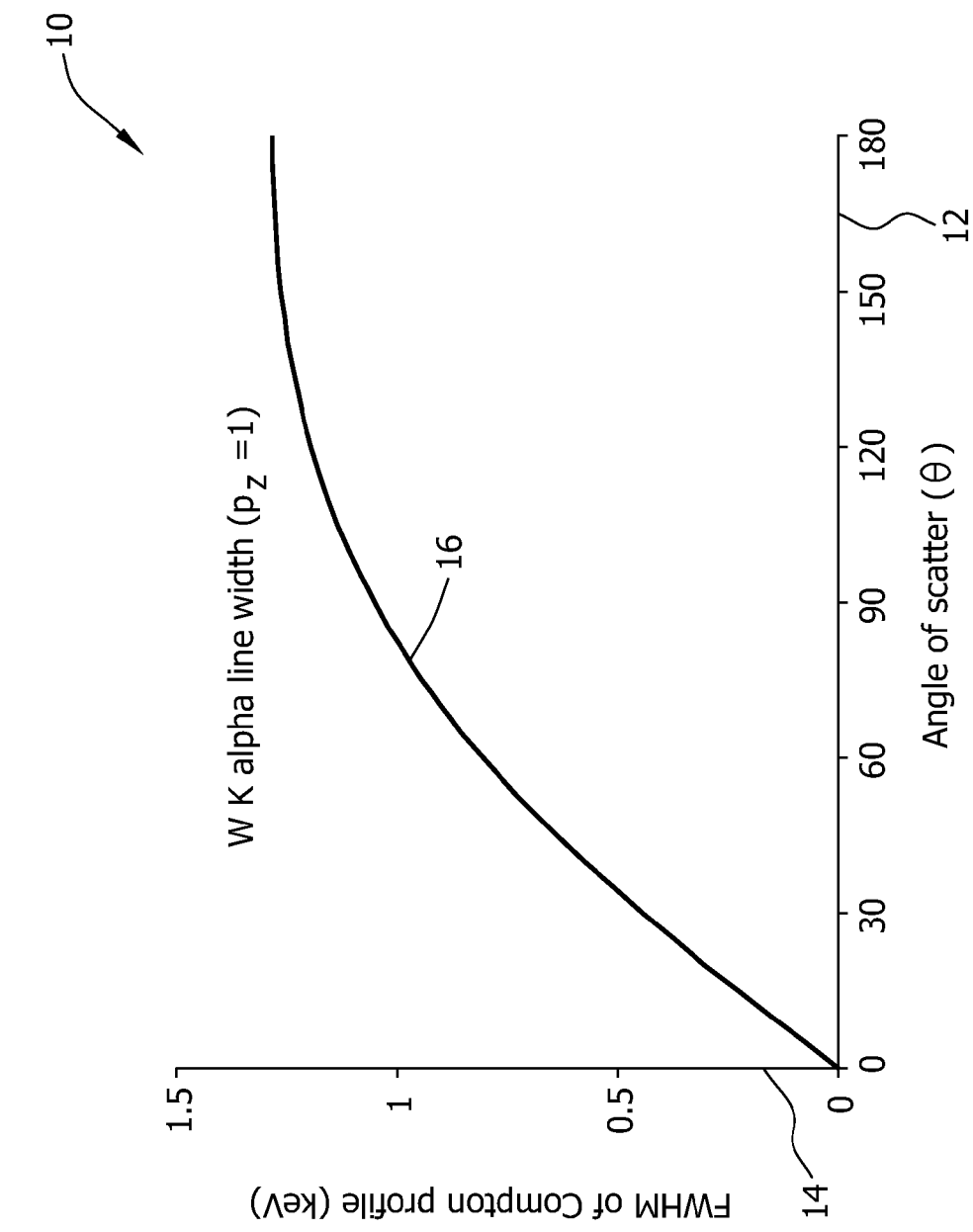
FIGS. 1-8 show exemplary embodiments of the system and method described herein.

FIG. 1 is a graph 10 of Compton peak width with respect to scatter angle when $p_z=1$, where $p_z$ is the Z component of electron momentum and is expressed in units of the ground state hydrogen atom momentum. An X-axis 12 of graph 10 shows an angle of scatter $\theta$ in degrees, and a Y-axis 14 of graph 10 shows an FWHM of a Compton profile in kilo-electronvolts (keV). In the exemplary embodiment, the FWHM in keV of a tungsten (W) $K\alpha1$ line (59.31 keV) scattered by an electron having unit mean momentum in atomic units (corresponding to a ground state of a hydrogen atom) is plotted against the angle of scatter, shown as a curve 16 in FIG. 1. When the FWHM of the W $K\alpha1$ line is plotted, it is evident that a Compton peak width is greatest for an angle of 180°. As such, when tungsten is used in an X-ray source, it is advantageous to select a relatively large angle of scatter $\theta$, such as equal to, or greater than, about 150°, to optimally resolve a shape of a profile Compton peak for an energy resolving detector having finite energy resolution.

Further, the embodiments described herein use an energy resolving detector that provides sufficient energy resolution to obtain the Compton profiles and/or $K\alpha$ lines described herein. A contemporary room temperature semiconductor detector, such as a Schottky contacted cadmium telluride (CdTe) detector, permits energy resolutions of about 1% at 60 keV in a relatively simple, reliable, and inexpensive detector module. Conventional energy resolving detectors cannot achieve such a resolution, and the methods described herein cannot efficiently be performed using such lower energy resolution detectors.

Figure 2:
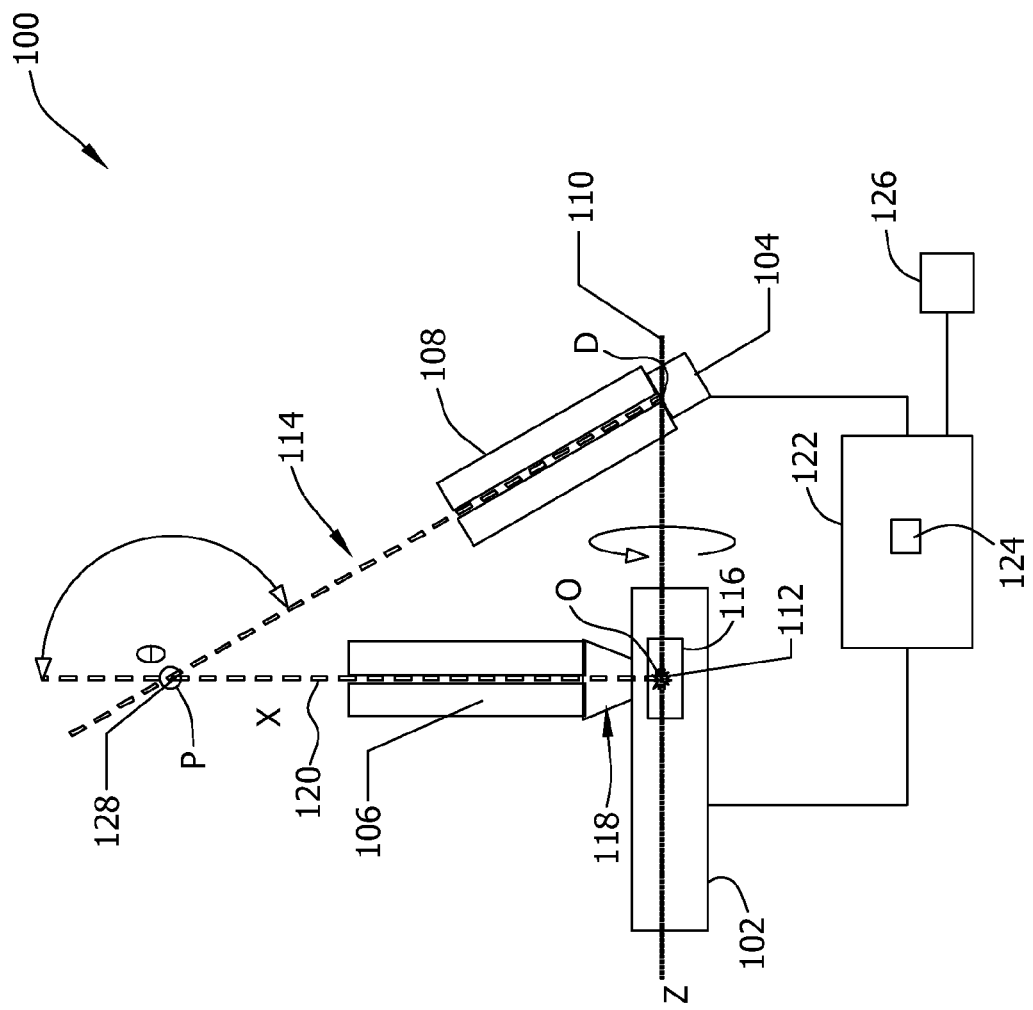

FIG. 2 is a schematic view of an exemplary X-ray system 100. More specifically, X-ray system 100 includes an X-ray source 102, an energy resolving detector 104, a primary collimator 106, and a secondary collimator 108. X-ray source 102 and energy resolving detector 104 are aligned on an axis of symmetry 110 such that a source focus 112 of X-ray source 102 and energy resolving detector 104 both lie on axis of symmetry 110. Primary collimator 106 and secondary collimators 108 are each rotationally symmetric about axis of symmetry 110. As used herein, the term "rotationally symmetric" refers to symmetry with respect to all rotations about an axis such that a cross-sectional shape of a rotationally symmetric object is substantially constant at any angle of rotation about the axis. Primary collimator 106 is aligned with source focus 112, and secondary collimator 108 is aligned with energy resolving detector 104. Secondary collimator 108 is configured to allow Compton scatter 114 at an angle $\theta$ to reach energy resolving detector 104.

Figure 3:
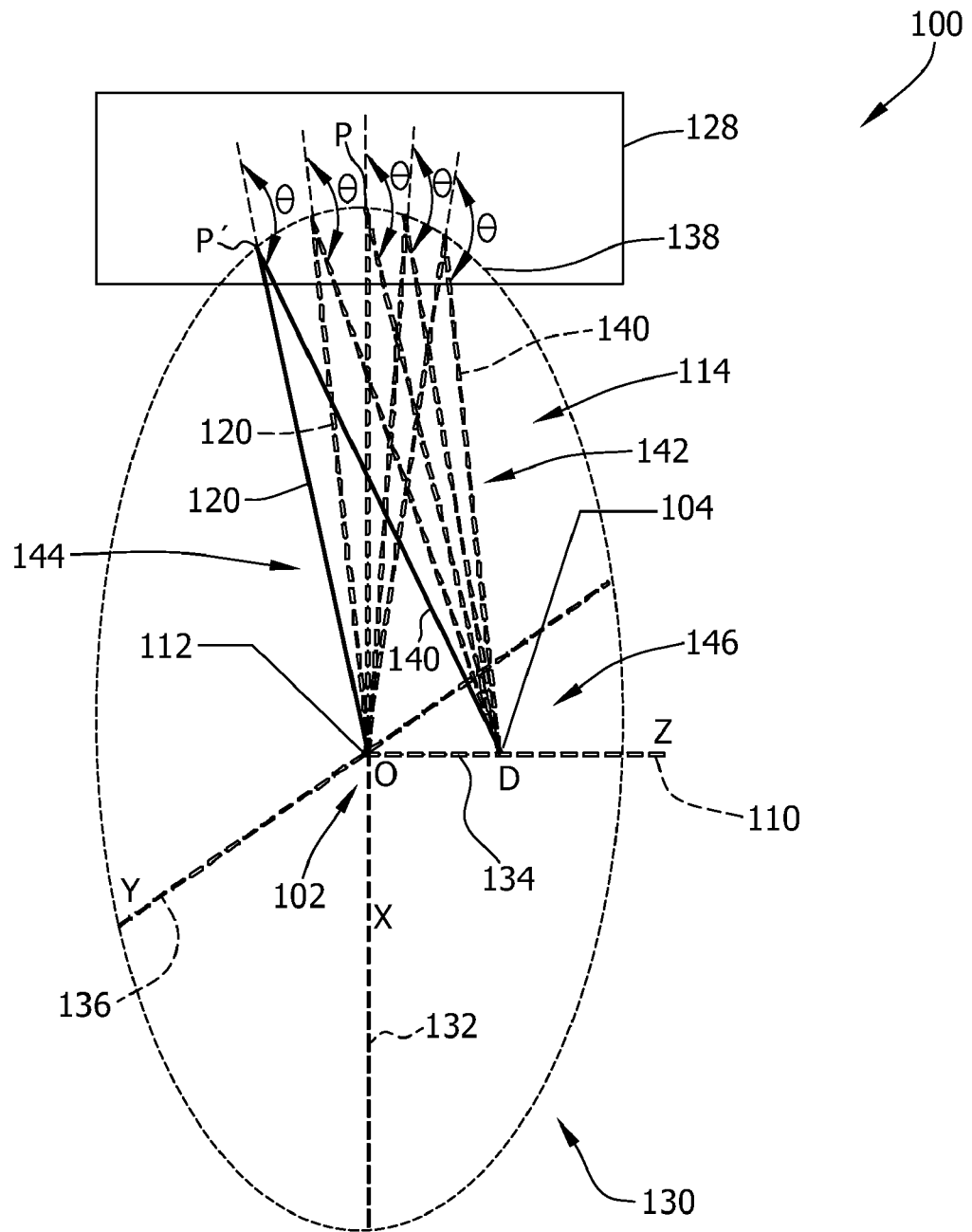

In the exemplary embodiment, X-ray source 102 is an electron impact x-ray tube with a tungsten anode 116 and is configured to generate X-rays 118. Alternatively, X-ray source 102 includes any anode that generates suitable $K\alpha$ lines that enable X-ray system 100 to function as described herein. In the exemplary embodiment, primary collimator 106 is configured to produce an X-ray beam 120 from X-rays 118 generated by X-ray source 102. More specifically, primary collimator 106 includes a moving diaphragm configured to select at least one pencil beam as X-ray beam 120 from a plurality of pencil beams that can be formed using primary collimator 106. As such, X-ray source 102 includes at least one source focus, including source focus 112. In one embodiment, as shown in FIG. 3, X-ray source 102 includes a plurality of source foci, including source focus 112. In a particular embodiment, primary collimator 106 includes a Nipkow type collimator and/or has a double helix "barber pole" arrangement to deflect an X-ray beam in a Y-direction. In an alternative embodiment, primary collimator 106 is any suitable collimator that enables X-ray system 100 to function as described herein. In the exemplary embodiment, energy resolving detector 104 is a spectroscopic detector, such as a Schottky-contacted CdTe detector, having an energy resolution of better than 2% FWHM at 60 keV photon energy. Alternatively, energy resolving detector 104 is any suitable detector that provides sufficient energy resolution to enable X-ray system 100 to function as described herein.

In the exemplary embodiment, as shown in FIG. 2, X-ray system 100 further includes a control system 122 that is operationally coupled with, such as in operational control communication with, X-ray source 102 and energy resolving detector 104. As used herein, "operational control communication" refers to a link, such as a conductor, a wire, and/or a data link, between two or more components of X-ray system 100 that enables signals, electric currents, and/or commands to be communicated between the two or more components. The link is configured to enable one component to control an operation of another component of X-ray system 100 using the communicated signals, electric currents, and/or commands.

Further, control system 122 is shown as being on device, however control system 122 may be a distributed system throughout X-ray system 100, an area surrounding X-ray system 100, and/or at a remote control center. Control system 122 includes a processor 124 configured to perform the methods and/or steps described herein. Further, many of the other components described herein include a processor. As used herein, the term "processor" is not limited to integrated circuits referred to in the art as a computer, but broadly refers to a controller, a microcontroller, a microcomputer, a programmable logic controller (PLC), an application specific integrated circuit, and other programmable circuits, and these terms are used interchangeably herein. It should be understood that a processor and/or control system can also include memory, input channels, and/or output channels.

In the embodiments described herein, memory may include, without limitation, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, input channels may include, without limitation, sensors and/or computer peripherals associated with an operator interface, such as a mouse and a keyboard. Further, in the exemplary embodiment, output channels may include, without limitation, a control device, an operator interface monitor and/or a display. In the exemplary embodiment, control system 122 is operationally coupled to a display device 126 for displaying an image generated using the methods and systems described herein.

Processors described herein process information transmitted from a plurality of electrical and electronic devices that may include, without limitation, sensors, actuators, compressors, control systems, and/or monitoring devices. Such processors may be physically located in, for example, a control system, a sensor, a monitoring device, a desktop computer, a laptop computer, and/or a distributed control system. RAM and storage devices store and transfer information and instructions to be executed by the processor(s). RAM and storage devices can also be used to store and provide temporary variables, static (i.e., non-changing) information and instructions, or other intermediate information to the processors during execution of instructions by the processor(s). Instructions that are executed may include, without limitation, imaging system control commands. The execution of sequences of instructions is not limited to any specific combination of hardware circuitry and software instructions.

During operation of X-ray system 100, control system 122 instructs X-ray source 102 to generate X-rays 118. X-rays 118 are collimated by primary collimator 106 to produce X-ray beam 120, such as a pencil beam, directed to interact with an object 128 to be scanned. X-ray beam 120 interacts with object 128 to produce at least Compton scatter 114, although it should be understood that transmission radiation and/or front scatter can also be produced by the interaction of X-ray beam 120 and object 128. Secondary collimator 108 collimates Compton scatter 114 such that Compton scatter 114 at angle θ is directed to energy resolving detector 104. Energy resolving detector 104 measures at least an intensity and energy of the photons in Compton scatter 114 reaching energy resolving detector 104. The measurements are transmitted to control system 122, and at least the detected energy is used by control system 122 to identify a material within object 128, as described in more detail below.

Figure 4:
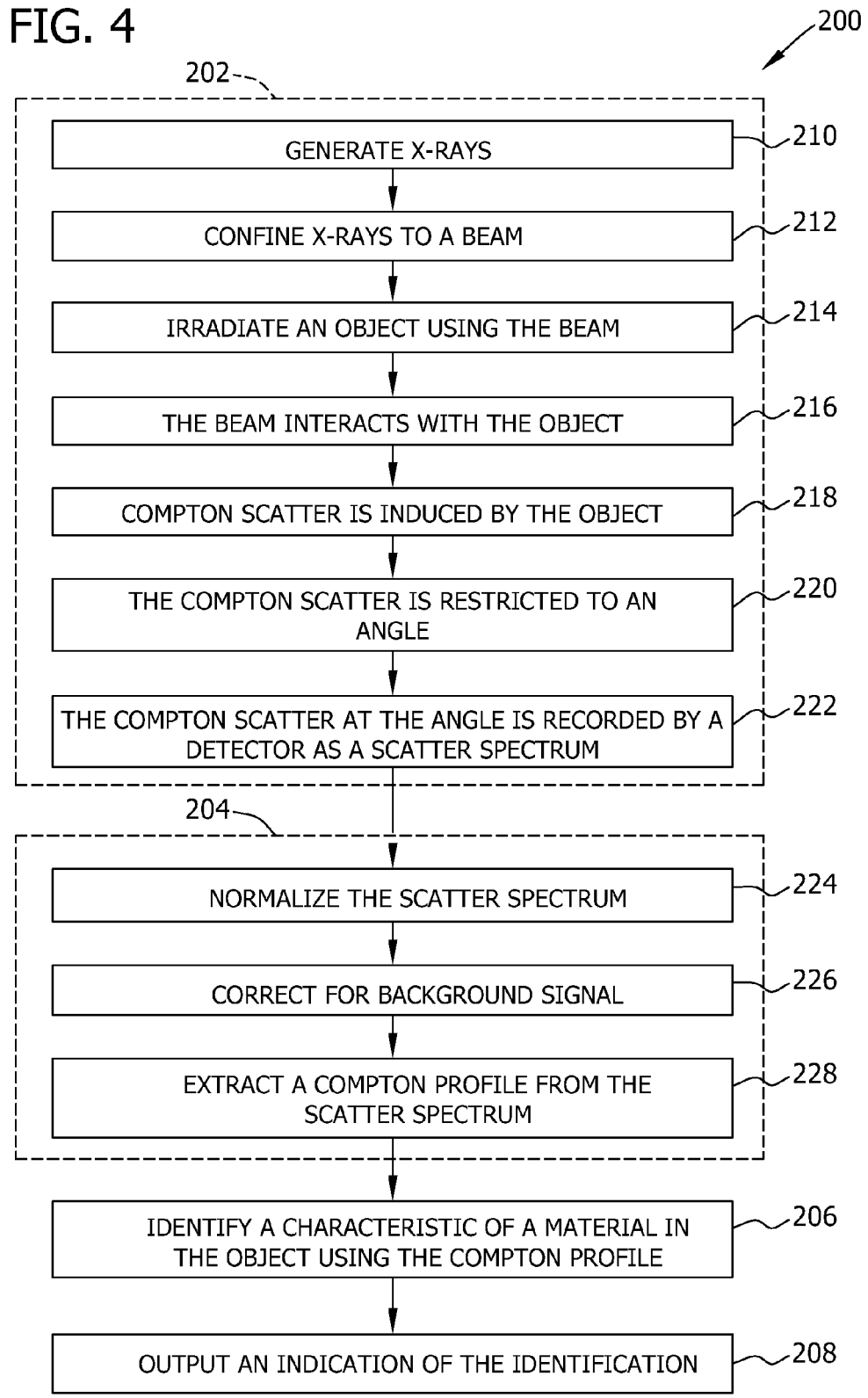
Figure 5:
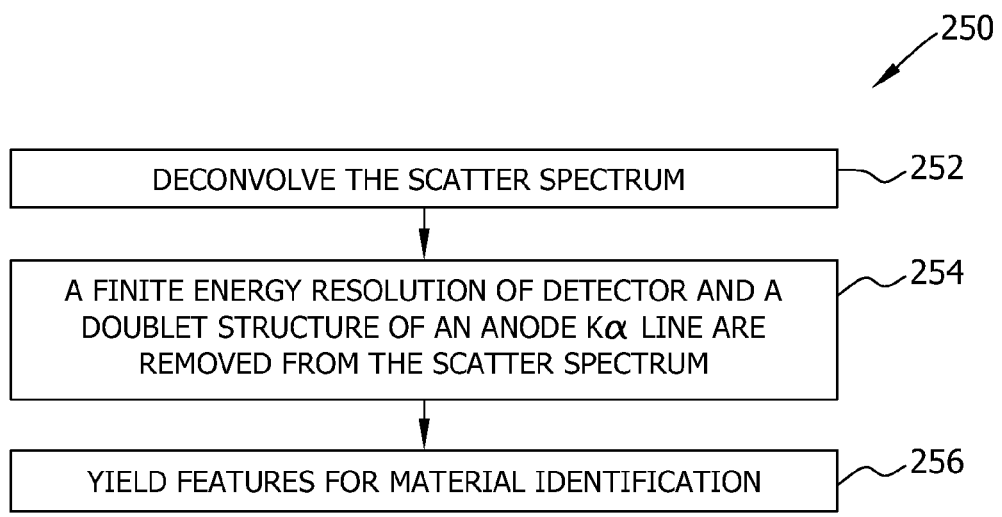
Figure 6:
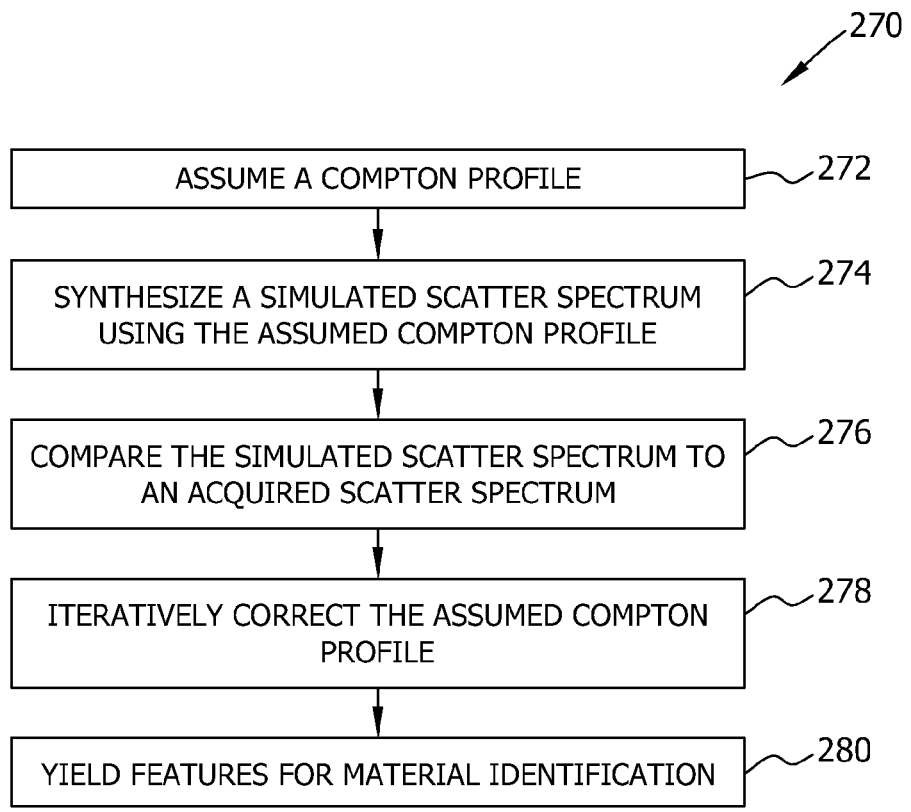

FIG. 3 is a schematic view of X-ray system 100 shown on an X-Y-Z coordinate system 130. Primary collimator 106 (shown in FIG. 2) is substantially parallel to an X-axis 132, axis of symmetry 110 is on a Z-axis 134, and a Y-axis 136 is perpendicular to X-axis 132 and Z-axis 134. FIG. 4 is a flowchart of a method 200 for performing material analysis with reflected inelastic scatter that may be used with X-ray system 100. FIG. 5 is a flowchart of an exemplary extraction process 250 that may be used with method 200. FIG. 6 is a flowchart of an alternative extraction process 270 that may be used with method 200.

Method 200 facilitates identifying and/or imaging a material and/or a substance within object 128. Control system 122 (shown in FIG. 2) performs method 200 by sending commands and/or instructions to components of X-ray system 100, such as X-ray source 102, energy resolving detector 104, and/or any other suitable component. Processor 124 (shown in FIG. 2) within control system 122 is programmed with one or more code segments configured to perform method 200. Alternatively, method 200 is encoded on a computer-readable medium that is readable by control system 122. In such an embodiment, control system 122 and/or processor 124 is configured to read computer-readable medium for performing method 200.

Referring to FIGS. 3 and 4, to perform a back scatter analysis of method 200, Compton scatter data is acquired 202, the acquired data is processed 204 to generate a Compton profile, and the Compton profile is used to identify 206 a characteristic of a material of object 128. In the exemplary embodiment, the Compton scatter data is a scatter spectrum. Further, an indication of the identification 206 can be output 208 to, for example, display device 126 (shown in FIG. 2).

More specifically, to acquire 202 Compton scatter data, X-rays 118 are generated 210 by X-ray source 102 and are collimated or confined 212 by primary collimator 106 to an arc containing the points O, P, and P', where a point P and a point P' lie on an arc 138 of a circle having a center at a point O. Point O represents a location of source focus 112 of X-ray source 102, and arc 138 on which point P and point P' lie extends at least partially through object 128 such that point P and point P' are located within object 128. Further, each point P and P' is a scatter voxel for producing a Compton profile and/or an image using Compton scatter 114. In the exemplary embodiment, a scan line is contained within an XY plane, and X-rays 118 are confined 212 to pencil beam 120 in the plane OPP'.

In the exemplary embodiment, primary collimator 106 is used to select from a fan OP'P of radiation a single pencil beam 120, ray OP', from source focus 112 with which to irradiate 214 object 128. A direction from point O toward point P or point P' is considered to be a direction of pencil beam 120. Moving a diaphragm of primary collimator 106 allows sequential selection of ray OP' and ray OP to irradiate 214 object 128, thus scanning pencil beam 120 across object 128. In one embodiment, object 128 is transported on a conveyor belt moving substantially parallel to Z-axis 134 in a Z direction to permit a two-dimensional (2D) scan of object 128. Alternatively, object 128 may be held stationary and X-ray source 102 and energy resolving detector 104 are moved relative to object 128 to acquire the 2D scan of object 128. For each location of pencil beam 120, for example ray OP' and ray OP, inelastic scatter interactions occur within object 128 and a Compton scatter ray P'D or PD, respectively, irradiates the detector. More specifically, when pencil beam 120 interacts 216 with object 128 at point P or point P', Compton scatter 114 is induced 218 by object 128. Compton scatter 114 includes a plurality of rays 140 of scattered radiation.

Compton scatter 114 induced 218 in object 128 is collimated or restricted 220 to paths lying on a surface 142 such that a predetermined angle of scatter OPD or θ is constant irrespective of which point P or P' is irradiated 214 by pencil beam 120. Angle OPD or θ is an angle defined between a direction of scatter, such as a ray PD or P'D, and the direction of pencil beam 120, such as ray OP or ray OP'. In the exemplary embodiment, angle θ, or angle OPD, is equal to, or greater than about 140°. For the condition of a constant angle θ to be met, source focus 112 and energy resolving detector 104 both lie on axis of symmetry 110, and primary collimator 106 and secondary collimator 108 are each rotationally symmetric around axis of symmetry 110. As shown in FIG. 3, source focus 112 at point O and energy resolving detector 104 at point D both lie on axis of symmetry 110, also shown as Z-axis 134. A sum of all primary beams 120 is contained in a planar fan 144, whereas rays 140 of Compton scatter 114 travel on a conical surface 142 and have paths that intersect a cone vertex 146. It should be understood that an axis of symmetry other than axis of symmetry 110 lying on Z-axis 134 may be used with X-ray system 100 as long as point O and point D are on the same axis of symmetry.

A back scatter energy spectrum of Compton scatter ray 140 is recorded 222 by energy resolving detector 104 at point D. Energy resolving detector 104 is an energy resolving (spectroscopic) detector that is a room temperature semiconductor detector, such as Schottky contacted CdTe detector, having resolution of at least 2% FWHM at 60 keV photon energy. Once a scatter spectrum has been recorded 222 from a certain object voxel, such as point P and/or point P', the scatter spectrum is processed 204 to correct for various effects. The recorded scatter spectrum includes Compton broadened characteristic line peaks based on the Kα lines of an anode material.

Processing 204 includes normalizing 224 a spectral region encompassing the characteristic line peaks to a continuous region of the scatter spectrum above and below a peak region. More specifically, Compton broadened Kα lines of tungsten range approximately from 54 keV to 64 keV (shown in FIGS. 7 and 8), and the Compton broadened Kα lines are normalized 224 to an integrated Compton scatter intensity between about 50 keV and a K absorption edge at about 70 keV. During normalization 224, a number of detected photons in each energy bin between 54 keV and 64 keV is divided by a total number of detected photons summed over all energy bins between 50 keV and 70 keV. Normalizing 224 accounts for system dependent factors, such as source intensity and/or detection solid angle, and self-attenuation of Compton scatter 114 within object 128 that produced Compton scatter 114.

Figure 8:
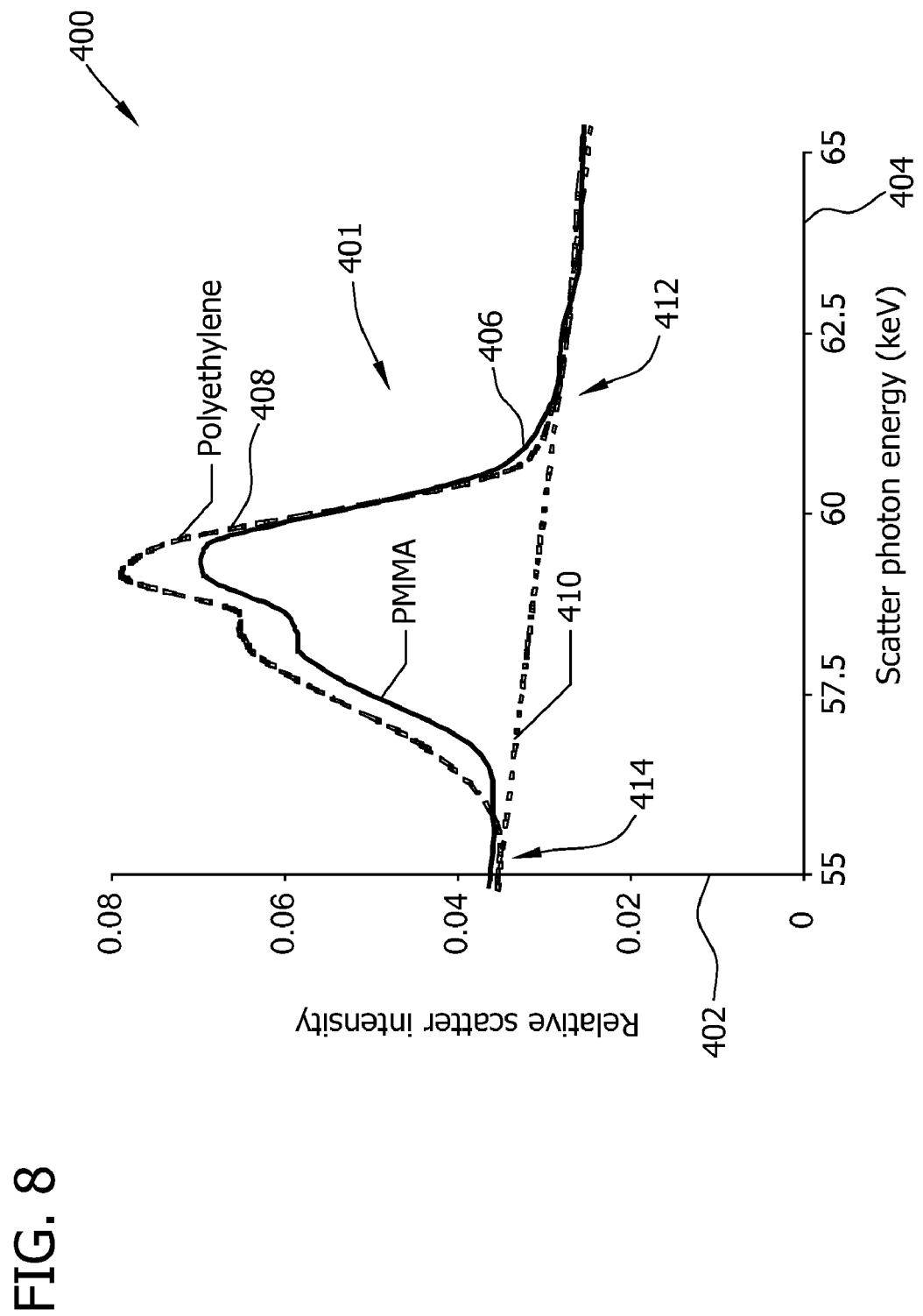

Processing 204 further includes correcting 226 for a background signal by removing a continuous bremsstrahlung background signal, such as bremsstrahlung background signal 410 for a polyethylene curve 408 as shown in FIG. 8, from the scatter spectrum. The bremsstrahlung background signal is estimated as a straight line and fitted to a high energy side and a low energy side of the characteristic line peaks of a curve. The estimated straight line is then removed from the scatter spectrum using, for example, a subtraction operation, to correct the scatter spectrum for the background signal. A Compton profile is then extracted 228 from the Compton scatter spectrum using, for example, method 250 (shown in FIG. 5) and/or method 270 (shown in FIG. 6).

From the Compton profile extracted by processing the scatter spectrum, a characteristic of a material of object 128 is identified 206. More specifically, in one embodiment, distinct shapes of the Kα lines in the Compton scatter spectrum can be matched to corresponding Kα line shapes of known materials that are, for example, stored in a library accessible to control system 122, to identify 206 a type and/or a chemical make-up of the material. In the exemplary embodiment, an indication of the identification 206 is output 208 by control system 122. For example, the Compton spectrum and/or the results of the identification can be output 208 to display device 126. In a particular embodiment, control system 122 is configured to output 208 an alarm if the identified material is on a list of alarm materials, such as explosives and/or narcotics. An image of object 128 can alternatively or additionally be output 208 to display device 126. The image can be produced using intensities of Compton scatter and/or intensities of transmitted radiation.

In the exemplary embodiment, as shown in FIG. 5, the Compton profile is extracted 250 by deconvolving 252 the scatter spectrum. More specifically, a finite energy resolution of energy resolving detector 104 and a doublet structure of the tungsten Kα line (Kα1 at 59.31 keV, and Kα2 at 57.973 keV) are removed 254 from the scatter spectrum using, for example, the Jansson/Van Cittert (JVC) iterative deconvolution algorithm. Several constraints can be built into the deconvolution algorithm including, for example, the restriction of known positions and/or known relative intensities of the Kα lines, and/or the restriction of the deconvolved Compton profile to a positive, symmetrical signal in a "q" space. To deconvolve the Compton profile into the "q" space, the data is transformed from an energy scale into a momentum scale. The Compton profile resulting from deconvolution 252 can be expressed as a sum of Gaussians, such as three Gaussians, each of which is characterized by a peak amplitude and a width. As such, deconvolution 252 yields 256 six features (i.e., three peak amplitudes and three widths corresponding to the three Gaussians) for material identification 206 and a total backscatter signal.

In an alternative embodiment, as shown in FIG. 6, the Compton profile is extracted 270 by assuming 272 a Compton profile for the scatter spectrum. An assumed Compton profile is used to synthesize 274 a simulated scatter spectrum. More specifically, in the exemplary embodiment, the simulated scatter spectrum is synthesized 274 as a superposition of, for example, three Gaussian functions, each having variable peak amplitude and width using, for example, the method described by Hindeleh and Johnson in "The Resolution of Multipeak Data in Fibre Science," *J. Phys. D: Appl. Phys.*, Vol. 4, pp 259-263 (1971). In one embodiment, a combination of Gaussians that minimizes a mean square error between the synthesized scatter spectrum and the acquired scatter spectrum is selected. As such, the detector energy resolution function is incorporated naturally in the data analysis.

The synthesized scatter spectrum is then compared 276 to the acquired scatter spectrum to produce a difference signal. In the exemplary embodiment, the assumed Compton profile is iteratively corrected 278 using the difference signal to produce a corrected Compton profile that is used as the extracted Compton profile. The extracted Compton profile yields 280 six features (i.e., three peak amplitudes and three widths corresponding to the three Gaussians) for material identification 206 and yields a total backscatter signal.

Figure 7:
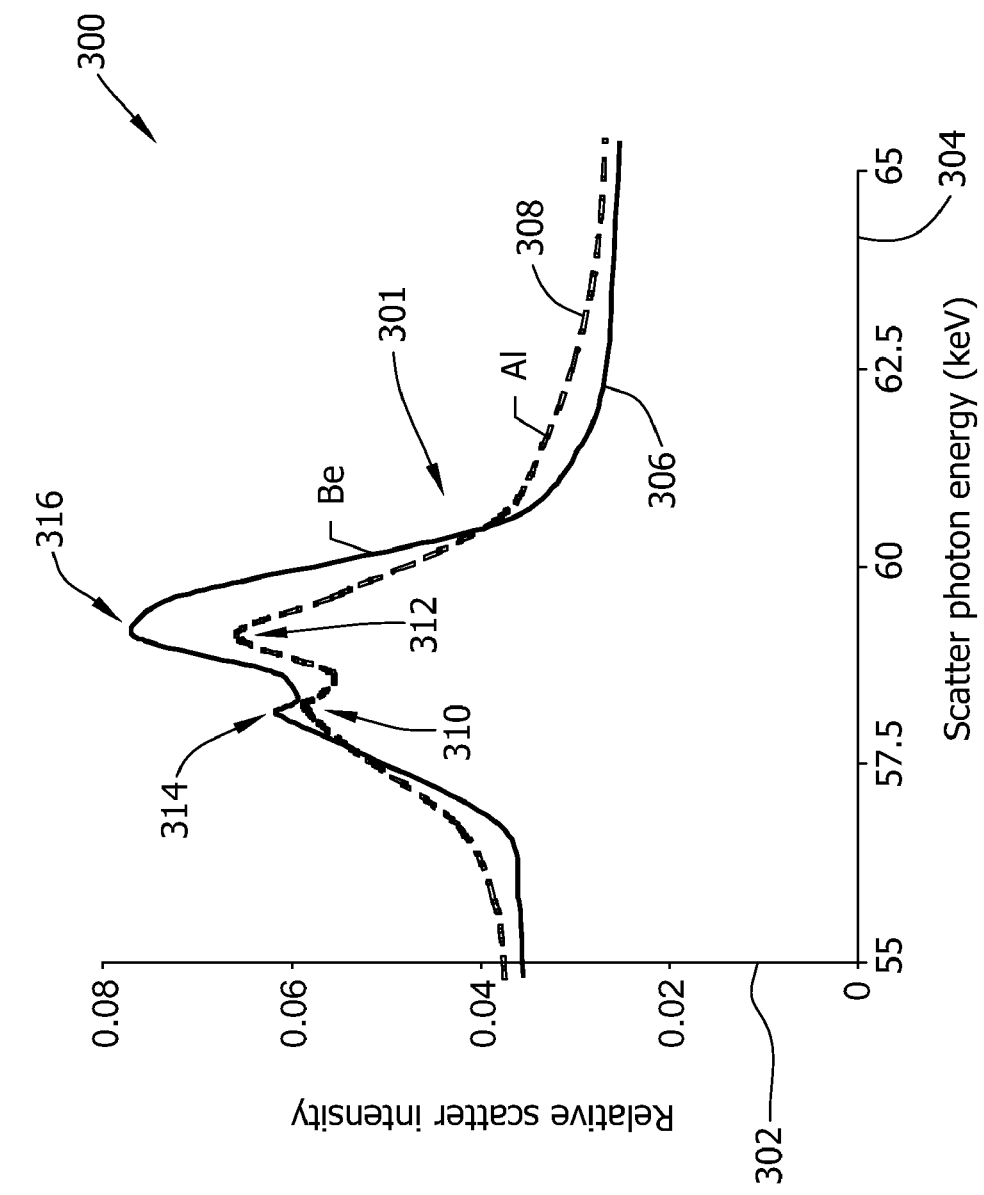

FIG. 7 is a graph 300 of a Compton scatter spectrum 301 of Beryllium (Be) and Aluminum (Al) that is used to produce a Compton profile an object including Be and Al. Compton scatter spectrum 301 may be obtained using X-ray system 100 (shown in FIG. 2) by scanning an object that includes Be and Al. The acquired scatter data is processed 204 (shown in FIG. 4) as described above to obtain a normalized Compton scatter spectrum from Compton scatter spectrum 301.

In graph 300, Compton scatter spectrum 301 is represented as a plot of relative scatter intensity with respect to scatter photon energy. The relative scatter intensity is plotted on a Y-axis 302 in arbitrary units, and the scatter photon energy is plotted on an X-axis 304 in keV. More specifically, graph 300 shows examples of 90° inelastic scatter from a tungsten anode X-ray tube irradiating Be and Al. Compton scatter spectrum 301 is normalized 224 (shown in FIG. 4) to a unit area between a low energy limit of 54 keV and a high energy limit of 72 keV. As such, differences in a Be curve 306 and an Al curve 308 arise from Compton profile line shape changes.

In Compton scatter spectrum 301, Al curve 308, a first peak 310 corresponds to a W Kα1 line and a second peak 312 corresponds to a W Kα2 line, which are incompletely resolved owing to the Doppler broadening effect. In Be curve 306, a first peak 314 corresponds to the W Kα1 line and a second peak 316 corresponds to a W Kα2 line. Peaks 314 and 316 of Be curve 306 have lower visibility as compared to peaks 310 and 312 of Al curve 308. In seeming contradiction to a better resolution of Al scatter, wings of Al peaks 310 and 312 are wider than wings of Be peaks 314 and 316. This apparent discrepancy can be accounted for by differing electronic configurations of Be and Al. In the exemplary embodiment, Al peaks 310 and 312 and Be peaks 314 and 316 are used to identify 206 (shown in FIG. 4) Al and Be, respectively, in object 128.

More specifically, as used herein the term "visibility" is a measurement of ability to discern a feature, such as a peak, surrounded by other structures in a spectrum. For example, when a peak-to-valley ratio is high, a Compton scatter spectrum includes a relatively large peak in relatively flat surroundings, which produces a relatively high visibility. When a valley between a $K\alpha1$ peak and a $K\alpha2$ peak is relatively shallow and the $K\alpha1$ peak and/or the $K\alpha2$ peak are relatively small in a Compton scatter spectrum, such as the $K\alpha1$ peak and the $K\alpha2$ peaks for Be, it may be more difficult to discern the $K\alpha1$ peak and/or the $K\alpha2$ peak from the surroundings, particularly in the presence of noise, which produces a relatively low visibility. As such, in general, the wider the Compton profile of a material is, the lower the $K\alpha1$ and/or $K\alpha2$ peaks and/or the shallower the valley in the Compton scatter spectrum becomes. However, although peaks 314 and 316 in Be curve 306 have lower visibility in Compton scatter spectrum 301 than peaks 310 and 312 in Al curve 308, a Compton profile of Be is narrower than a Compton profile of Al.

Such an apparent discrepancy can be accounted for by differing electronic configurations of Be and Al. More specifically, an electronic configuration of Be, which includes two loose valence electrons and two tight core electrons, produces a Compton profile that is similar to a single Gaussian curve with a single width. However, an electronic configuration of Al, which includes three loose valence electrons and eight tight core electrons, produces a Compton profile that is similar to two Gaussian curves with one high, narrow curve sitting on another low, wide curve. As such, the Compton profile of Al is wider than the Compton profile of Be although Be peaks 314 and 316 are less visible than Al peaks 310 and 312 in Compton scatter spectrum 301.

FIG. 8 is a graph 400 of a Compton scatter profile 401 of a Poly(methyl methacrylate) (PMMA) material, such as LUCITE® ("Lucite" is a registered trademark of Lucite International, Inc., South Hampton, United Kingdom) and polyethylene that may be generated using X-ray system 100 (shown in FIG. 2). In the exemplary embodiment, object 128 (shown in FIG. 2) includes the PMMA material and polyethylene and is scanned using X-ray system 100. The acquired scatter data is processed 204 (shown in FIG. 4) as described above to obtain a normalized Compton scatter spectrum from Compton scatter profile 401. Compton scatter spectrum 401 is represented in graph 400 as a plot of relative scatter intensity with respect to scatter photon energy. The relative scatter intensity is plotted on a Y-axis 402 in arbitrary units, and the scatter photon energy is plotted on an X-axis 404 in keV.

Compton scatter spectrum 401 includes a PMMA curve 406, a polyethylene curve 408, and continuous bremsstrahlung component 410. To generate a Compton profile from Compton scatter spectrum 401, PMMA curve 406 and polyethylene curve 408 are individually normalized 224 (shown in FIG. 4) to have a substantially equal unit area. As such, any significant difference evident between PMMA curve 406 and polyethylene curve 408 originates solely in varying electron momentum distributions. Continuous bremsstrahlung component 410 is estimate as a straight line and fit to a high energy side 412 and a low energy side 414 of polyethylene curve 408. Method 200 is used to generate a Compton profile from Compton scatter spectrum 401.

The above-described embodiments provide measurable Compton broadening in a scatter spectrum induced by K characteristic lines, such as $K\alpha$ lines, of an anode of an X-ray tube. The Compton broadening described herein facilitates designing a diagnostic tool, such as an X-ray system, that is sensitive to electron momenta differences in samples of interest. Such a diagnostic tool could be implemented in non-destructive testing (NDT) applications. Further, the above-described embodiments provide a Compton imaging spectrometer, such as the X-ray system described herein, which can be applied to "in situ" analysis and imaging of plastic composites and/or metals that are inspected in process monitoring, plastic recycling, and/or aircraft construction industries.

Further, the above-described Compton profiles readily distinguish among plastics, ceramics, metals, and/or human tissues, which facilitates reducing a false alarm rate in, for example, security screening, personnel screening, and/or container inspection, as compared to systems that do not produce a Compton profile of an object being scanned. Moreover, the embodiments described herein provide a material sensitive technique that can be applied in the recycling industry for rapidly and cheaply separating plastics. Finally, the Compton profiles described herein enable enhanced non-destructive inspection and/or testing of plastic composites in the aircraft industry. In such applications, back scatter geometry is especially useful for analyzing superficial regions of plastics, such as near or at a surface of a plane, that cannot otherwise be inspected with traditional radiography.

Moreover, the embodiments described herein provide molecular specific imaging without including both a back scatter detector and a front scatter detector. More specifically, the above-described embodiments provide molecular specific imaging based on energies of back scatter radiation. As such, the embodiments described herein are more cost-effective than systems having both back scatter detectors and front scatter detectors.

A technical effect of the system and method described herein includes at least one of: (a) generating an X-ray beam using an X-ray source having an anode; (b) acquiring a scatter spectrum from Compton scatter produced when the X-ray beam interacts with the object, wherein the scatter spectrum is acquired using an energy resolving detector; (c) extracting a Compton profile from the scatter spectrum by processing the scatter spectrum using a control system of the X-ray system, wherein the Compton profile includes peaks at characteristic lines of the anode; (d) identifying a characteristic of a material of the object using the Compton profile; and (e) outputting an indication of the characteristic of the material.

Exemplary embodiments of method and system for performing materials analysis with reflected inelastic scatter are described above in detail. The method and system are not limited to the specific embodiments described herein, but rather, components of the system and/or steps of the method may be utilized independently and separately from other components and/or steps described herein. For example, the method may also be used in combination with other imaging systems and methods, and is not limited to practice with only the X-ray system and method as described herein. Rather, the exemplary embodiment can be implemented and utilized in connection with many other radiation imaging applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for performing materials analysis of an object using an X-ray system, said method comprising:
   generating an X-ray beam using an X-ray source having an anode;
   acquiring a scatter spectrum from Compton scatter produced when the X-ray beam interacts with the object, the scatter spectrum acquired using an energy resolving detector;
   extracting a Compton profile from the scatter spectrum by processing the scatter spectrum using a control system of the X-ray system, the Compton profile including peaks at characteristic lines of the anode;
   identifying a characteristic of a material of the object using the Compton profile; and
   outputting an indication of the characteristic of the material.

2. A method in accordance with claim 1, wherein acquiring a scatter spectrum from Compton scatter comprises:
   irradiating the object with a pencil beam;
   collimating the Compton scatter to be a predetermined angle with respect to a direction of the pencil beam; and
   recording the scatter spectrum of the Compton scatter at the predetermined angle using the energy resolving detector.

3. A method in accordance with claim 1, wherein extracting a Compton profile comprises:
   normalizing the scatter spectrum;
   correcting the normalized scatter spectrum by removing a background signal from the normalized scatter spectrum; and
   extracting the Compton profile from the normalized and corrected scatter spectrum.

4. A method in accordance with claim 3, wherein normalizing the scatter spectrum comprises dividing a number of detected photons in each energy bin within a first predetermined range by a total number of detected photons summed over a plurality of energy bins within a second predetermined range that is different than the first predetermined range.

5. A method in accordance with claim 1, wherein extracting a Compton profile comprises:
   deconvolving the scatter spectrum;
   removing a finite energy resolution of the energy resolving detector and a doublet structure of the characteristic lines of the anode from the scatter spectrum; and
   yielding features of the scatter spectrum for material identification.

6. A method in accordance with claim 1, wherein extracting a Compton profile comprises:
   assuming a Compton profile for the acquired scatter spectrum;
   synthesizing a simulated scatter spectrum from the assumed Compton profile;
   comparing the simulated scatter spectrum with the acquired scattered spectrum to produce a difference signal;
   iteratively correcting the assumed Compton profile using the difference signal to produce a corrected Compton profile; and
   yielding features of the scatter spectrum for material identification based on the corrected Compton profile.

7. A method in accordance with claim 6, wherein synthesizing a simulated scatter spectrum from the assumed Compton profile comprises superposing a predetermined number of Gaussian functions.

8. A method in accordance with claim 1, wherein extracting a Compton profile comprises:
   processing the scatter spectrum using a plurality of Gaussians, each Gaussian of the plurality of Gaussians including a peak amplitude and a width; and
   yielding features of the scatter spectrum for material identification based on the peak amplitudes and the widths of the plurality of Gaussians.

9. An X-ray system for analyzing an object, said X-ray system comprising:
   an X-ray source comprising an anode and at least one source focus, said X-ray source configured to generate an X-ray beam at said at least one source focus, said anode configured to generate characteristic lines;
   an energy resolving detector positioned with respect to said at least one source focus, said energy resolving detector configured to record Compton scatter produced from the X-ray beam interacting with the object, the Compton scatter at an angle to a direction of the X-ray beam; and
   a control system operationally coupled to said X-ray source and said energy resolving detector, said control system configured to:
      acquire a scatter spectrum from the Compton scatter using said energy resolving detector;
      extract a Compton profile from the scatter spectrum by processing the scatter spectrum, the Compton profile including peaks at the characteristic lines of said anode; and
      identify a characteristic of a material of the object using the Compton profile.

10. An X-ray system in accordance with claim 9, further comprising a primary collimator configured to produce sequentially a plurality of pencil beams from a source focus to scan the object.

11. An X-ray system in accordance with claim 9, further comprising a secondary collimator configured to collimate the Compton scatter to be at the angle for detection by said energy resolving detector.

12. An X-ray system in accordance with claim 9, wherein said anode comprises a tungsten (W) anode that generates a W Kα1 line and a W Kα2 line as the characteristic lines.

13. An X-ray system in accordance with claim 9, wherein said energy resolving detector comprises a Schottky contacted cadmium telluride (CdTe) detector configured to provide energy resolutions of about 1% full width at half maximum (FWHM) at 60 kilo-electronvolts (keV).

14. An X-ray system in accordance with claim 9, wherein said energy resolving detector comprises a semiconductor detector configured to provide an energy resolution greater than 2% FWHM at 60 keV.

15. An X-ray system in accordance with claim 9, wherein a Z-axis of said X-ray system defines an axis of symmetry, said at least one source focus and said energy resolving detector positioned on said axis of symmetry.

16. An X-ray system in accordance with claim 9, further comprising:
   an axis of symmetry; and
   a primary collimator configured to produce a pencil beam at said at least source focus, said primary collimator rotationally symmetric about said axis of symmetry.

17. An X-ray system in accordance with claim 9, further comprising:
   an axis of symmetry; and a secondary collimator configured to collimate the Compton scatter to be at the angle, said secondary collimator rotationally symmetric about said axis of symmetry.

18. An X-ray system in accordance with claim 9, wherein the angle is at least 150°.

19. An X-ray system in accordance with claim 9, wherein said control system is further configured to:

normalize the scatter spectrum;

correct the normalized scatter spectrum by removing a background signal from the normalized scatter spectrum; and extract the Compton profile from the normalized and corrected scatter spectrum.

20. An X-ray system in accordance with claim 9, wherein said control system is further configured to:

process the scatter spectrum using a plurality of Gaussians, each Gaussian of the plurality of Gaussians including a peak amplitude and a width; and yield features of the scatter spectrum for material identification based on the peak amplitudes and the widths of the plurality of Gaussians.

* * * * *